United States Patent [19]

Latham, Jr.

[11] 4,086,924
[45] May 2, 1978

[54] PLASMAPHERESIS APPARATUS

[75] Inventor: Allen Latham, Jr., Jamaica Plain, Mass.

[73] Assignee: Haemonetics Corporation, Natick, Mass.

[21] Appl. No.: 730,106

[22] Filed: Oct. 6, 1976

[51] Int. Cl.$^2$ .................... A61M 5/00; A61M 1/03
[52] U.S. Cl. ............................. 128/214 R; 128/214 E
[58] Field of Search .......... 128/214 R, 214 D, 214 B, 128/214 E, 214 F, 214.2, 272; 233/1 R, 19 R

[56] References Cited

U.S. PATENT DOCUMENTS

| | | | |
|---|---|---|---|
| 3,140,714 | 7/1964 | Murphy et al. | 128/214 R |
| 3,145,713 | 8/1964 | Latham | 128/214 R |
| 3,459,182 | 8/1969 | Naftulin | 128/214 R |
| 3,489,145 | 1/1970 | Judson et al. | 128/214 R |
| 3,610,226 | 10/1971 | Albisser | 128/214 R X |
| 3,916,892 | 11/1975 | Latham | 128/214 R |

*Primary Examiner*—Dalton L. Truluck
*Attorney, Agent, or Firm*—David E. Brook

[57] ABSTRACT

Plasmapheresis apparatus is disclosed which comprises a unique combination of blood withdrawal, separation and return means, together with automatic cycle control means. This apparatus can withdraw whole blood from a donor, separate it into plasma and non-plasma components, and return the non-plasma component to the donor while the donor remains connected to the apparatus throughout the entire procedure. Standard quantities of separated plasma can be obtained in significantly reduced times, and the possibility of mistakenly returning wrong blood components to the donor is eliminated.

9 Claims, 7 Drawing Figures

PLASMAPHERESIS APPARATUS

BACKGROUND OF THE INVENTION

1. Field of the Invention

This invention is in the field of blood processing and more specifically relates to plasmapheresis.

2. Description of the Prior Art

Whole human blood includes at least three types of specialized cells. These are the red blood cells, white blood cells, and platlets. All of these cells are suspended in plasma, a complex aqueous solution of proteins and other chemicals.

Until relatively recently, blood transfusions have been given using whole blood. There is, however, growing acceptance within the medical profession for transfusing only those blood components required by a particular patient instead of using a transfusion of whole blood. Transfusing only those blood components necessary preserves the available supply of blood, and in many cases, is better for the patient. Before blood component transfusions can be widely employed, however, satisfactory blood separation techniques and apparatus must evolve.

Plasmapheresis is the separation of whole blood into a plasma component and a non-plasma component under conditions whereby the plasma component is retained and the non-plasma component is returned to the donor. Presently, plasmapheresis is achieved on a large scale using satellite pouch systems. A variety of satellite pouch plasmapheresis systems have been patented, and some typical examples are those systems described in U.S. Pat. No. 3,190,546 to Raccuglia et al.; U.S. Pat. No. 3,211,368 to Shanley; and U.S. Pat. No. 3,545,671 to Ross. With such systems, whole blood is withdrawn from a donor and flows to a pouch containing anticoagulant. The pouch is then disconnected from the donor phlebotomy line, centrifuged, and the supernatant plasma fraction is expressed into a connected plasma pouch. The pouch containing the non-plasma component is then reconnected to the phlebotomy system so that the non-plasma component can be returned to the donor.

It has become customary with satellite pouch systems to carry out this sequence of steps twice for each donor. Typically, one unit, or about 500 ml. of whole blood, is withdrawn, anticoagulated and separated. Approximately 250 ml. of plasma component is obtained and the non-plasma component is returned to the donor. Subsequently, another unit of whole blood is withdrawn and processed. Using such techniques with satellite pouch systems, it takes approximately 85 minutes to obtain 500 ml. of separated plasma component and to return the non-plasma component to the donor. Because the blood pouch is disconnected from the donor at the end of each withdraw cycle, there is always the danger of returning blood components to a donor which are not his own. Satellite pouch systems also require careful attention during each of the processing cycles to produce consistently high quality plasma.

SUMMARY OF THE INVENTION

This invention relates to a new and unique plasmapheresis apparatus.

In this apparatus, whole blood is withdrawn from a donor using a phlebotomy needle and pressure cuff, or other similar means for withdrawing whole blood. Means for supplying anticoagulant to the withdrawn blood introduce an anticoagulant into the whole blood and the anticoagulated withdrawn whole blood is then transported by a blood pump, or other suitable means for transporting, to means for separating it into a plasma and a non-plasma component. A preferred means for separating comprises a plasmapheresis centrifuge, and, in particular, a new and unique plasmapheresis centrifuge as described infra. Separated plasma is stored in a plasma container and means are provided in the apparatus for detecting when a predetermined quantity of separated plasma component has been obtained. When this predetermined quantity of plasma component has been obtained, cycle control means immediately switch from the withdraw cycle to a return cycle in response to a signal received from the means for detecting. Means for monitoring when the non-plasma component has been returned to the donor are provided, and a preferred means for monitoring comprises a flexible, distendable monitor pouch. Cycle control means also immediately switch from the return cycle to either a withdraw cycle or a stand-by cycle in response to a signal received from the means for monitoring indicating that the return has been completed.

The plasmapheresis apparatus described herein significantly reduces the time required to complete a plasmapheresis separation. The reversal of blood or blood-component flow through the system is carried out automatically, and occurs so quickly that no saline drip is required to maintain patency in the blood path. Since the system is connected to the donor throughout the plasmapheresis procedure, any possibility of accidentally reinfusing blood components drawn from anyone except the donor is eliminated. Further, the system is fully integrated and sterile, and all pathways contacted by donor blood are used only for one donor. There are also significant safety features built into the apparatus to prevent reinfusion of blood components having entrained gas therein. Consistently high quality plasma can be obtained using the plasmapheresis apparatus of this invention, and no deleterious effects which are detectable are produced in either the plasma or non-plasma component.

DESCRIPTION OF PREFERRED EMBODIMENTS

The preferred embodiments of this invention can be described in more detail with reference to the FIGS.

Figure 1:
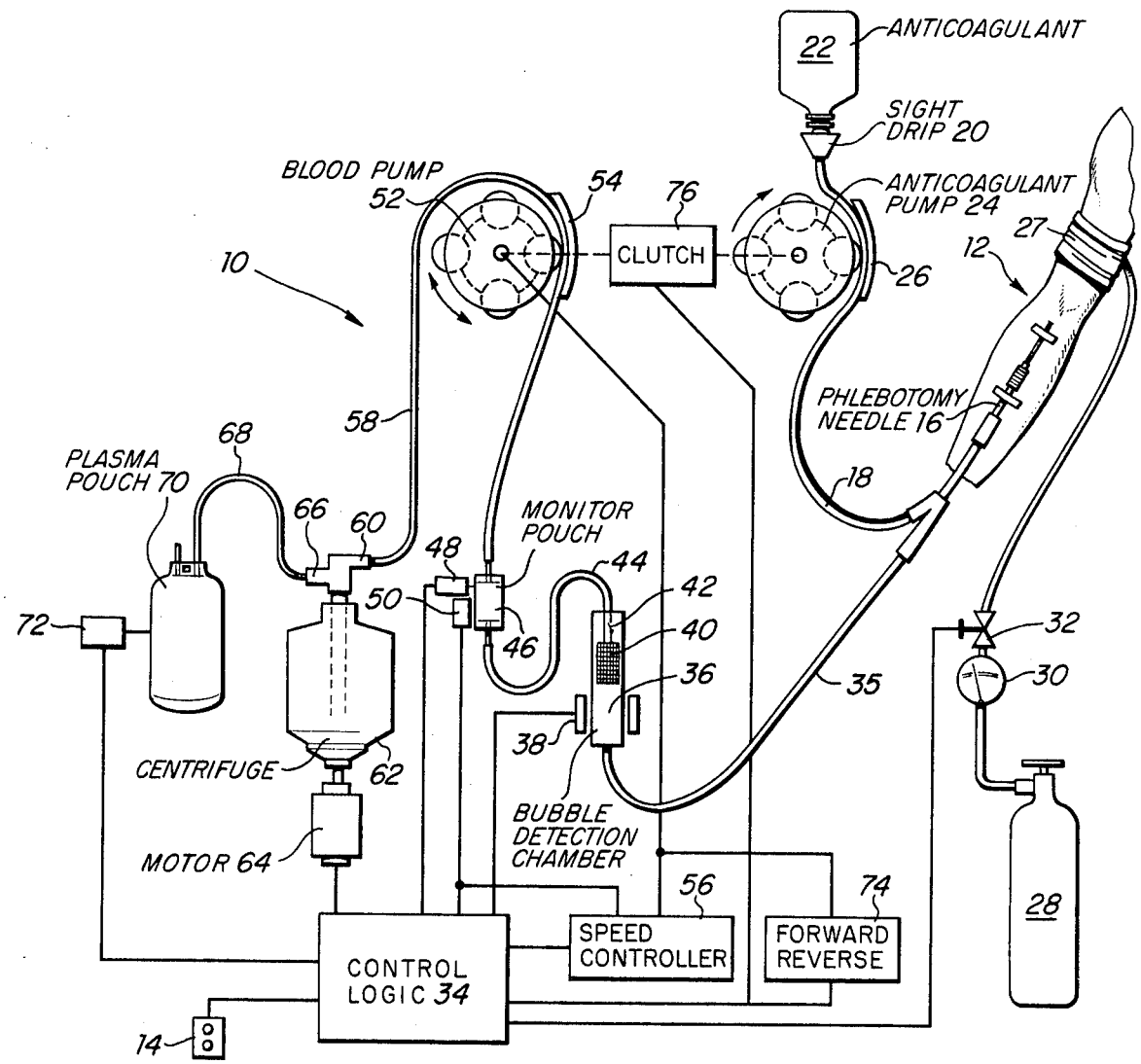
FIG. 1 is a diagramatic illustration of a plasmapheresis apparatus of this invention.

A diagramatic illustration of a suitable plasmapheresis apparatus 10 is shown in FIG. 1 together with a donor's arm 12. Plasmapheresis apparatus 10 is provided with a switch 14, which has an ON and an OFF button.

A standard phlebotomy needle 16 is used in this apparatus. Phlebotomy needle 16 might be, for example, a 15-guage, thin wall phlebotomy needle of the type which has a supply of anticoagulant connected to it so that freshly withdrawn blood is anticoagulated as soon as it leaves the needle. One specific type of suitable phlebotomy needle is described in detail in issued U.S. Pat. No. 3,916,892 to Latham.

Anticoagulant is supplied to phlebotomy needle 16 through tubing 18 which is connected through a sight drip 20 to pouch 22 containing anticoagulant. Anticoagulant pump 24 is a roller-type pump having a moveable platen 26 which clamps tubing 18 against the rollers of pump 24 when it is in its closed position. Roller pumps of this type are described in detail in U.S. Pat. No. 3,565,286.

Prior to making the venipuncture, phlebotomy needle 16 is primed with anticoagulant by opening platen 26 so that the rollers of anticoagulant pump 24 do not apply their pumping pressure pulses to tubing 18. With platen 26 in the open position, the outlet of anticoagulant pouch 22 is opened without interfering with the sterility of the system, usually by popping out a small round ball at its neck using mere thumb pressure. After a small amount of anticoagulant flows into sight drip 20, it is manually squeezed in a manner which expresses air into anticoagulant pouch 22 and thereafter provides a small reservoir of anticoagulant in sight drip 20. This small reservoir of anticoagulant provides assurance that the system is fully primed so that entrained gas bubbles cannot flow through the system to phlebotomy needle 16. It also provides visual assurance to operators that anticoagulant is mixing with whole blood leaving phlebotomy needle 16 is a predetermined ratio.

The site where the venipuncture is to be made is then prepared. After that, pressure cuff 27 is fastened around donor's arm 12 at a location above where phlebotomy needle 16 is to be inserted. Pressurizing gas, such as Freon ®, is supplied to pressure cuff 27 from gas canister 28, and the precise pressure applied is regulated by pressure regulator 30. A valve 32 may also be provided which has an open, a closed, and a relief position, the latter being provided to release pressure in cuff 27. A typical pressure is about 50 mm Hg which raises the pressure in the donor's veins sufficiently to facilitate the venipuncture and to boost blood flow from the donor's veins.

Plasmapheresis apparatus is now started by depressing the ON button of switch 14, which energizes the electrical systems, starts pump motors, activates detectors, etc. It also causes control logic 34 to advance to the first withdraw cycle which automatically opens valve 32 so that pressurizing gas flows to pressure cuff 27. Control logic 34 is used to monitor and control the overall operation of plasmapheresis apparatus 10, and might be, for example, a stepping switch or one or more solid state devices.

Anticoagulant pump platen 26 is then closed thereby clamping tubing 18 into anticoagulant pump 24 and initiating pumping action. At this point, the venipuncture is made by inserting phlebotomy needle 16 into one of the donor's veins at the previously prepared site.

Freshly withdrawn, anticoagulated, whole blood flows under venipressure from the donor through tubing 35 into the bottom of bubble detection chamber 36. Bubble detection chamber 36 has associated with it sonic transducers 38 and internal filter 40, which will be described in greater detail in conjunction with the return cycle. There may also be a check valve 42 provided to allow whole blood to by-pass filter 40 on the withdraw cycle.

Withdrawn blood then passes through tubing 44 into the bottom of monitor pouch 46. Monitor pouch 46 has both a weight detector 48 and a pressure detector 50 associated with it. Weight detector 48 is used to sense the weight of blood which is present in monitor pouch 46 at any given time. This, in turn, is used to both activate and to control the speed of blood pump 52, which is also a roller-type pump having a moveable platen 54, but which also can be operated in reverse. The function of pressure detector 50 will be described in conjunction with the return cycle.

At the start of a withdraw cycle, monitor pouch 46 is, of course, empty insofar as blood components are concerned. As blood enters pouch 46, its weight eventually reaches a threshhold value which is sensed by weight detector 48. At this weight, an appropriate signal is transmitted to control logic 34 which acts in response thereto to actuate blood pump 52 in the forward direction. Blood pump 52 preferably has at least two speeds, and these speeds are determined by speed controller 56 acting in response to signals received from weight detector 48. If the blood flow from phlebotomy needle 16 is greater than that to pump 52, monitor pouch 46 fills thereby becoming heavier and causing weight detector 48 to transmit signals to control logic 34 and speed controller 56 to advance blood pump 52 to its higher speed position. If, on the other hand, blood flow from phlebotomy needle 16 is less than that to the pump 52, monitor pouch 46 begins to empty thereby losing weight and causing signals to be transmitted to control logic 34 and speed controller 56 to return pump 52 to its lower speed position. If monitor pouch 46 continues to lose weight even at the lower pump speed, a signal is likewise transmitted to control logic 34 which responds by causing blood pump 52 to be shut off entirely until the monitor pouch fills once again. In this way, blood is pumped from monitor pouch 46 but never from the donor. This pattern of action continues throughout the withdraw cycle.

Anticoagulated whole blood is now pumped through tubing 58 to center inlet 60 of centrifuge bowl 62. Whole blood is separated in centrifuge bowl 62 into plasma and non-plasma components. Typically, centrifuge bowl 62 might be spun by motor 64, for example, at about 4800 r.p.m. The plasma component exits through outlet 66 and is transported via tubing 68 to plasma pouch 70. Weight detector 72 is used to determine the weight of accumulated plasma component in pouch 70. When some predetermined quantity has been collected, it transmits a signal to control logic 34, which causes the apparatus to advance to the return cycle. A typical withdraw cycle might consist, for example, of the withdrawal of about 500 ml. of whole blood and its separation into approximately 250 ml. of plasma with a small amount of anticoagulant. The non-plasma component remaining in centrifuge bowl 62 would typically consist of something like about 84% red cells and about 16% plasma, and would also contain a small amount of anticoagulant. As can be appreciated, then, the plasma component is essentially free of other components, while the non-plasma component is very rich in red blood cells, etc., but does contain some plasma as the necessary suspension medium.

As soon as the predetermined quantity of plasma has been collected, control logic 34, in response to a signal from weight detector 72, immediately switches to a return cycle. This is achieved by braking centrifuge bowl 62 to a complete stop, switching blood pump 52 into its reverse pumping mode through forward-reverse switch 74, relieving pressure cuff 27 by turning valve 32 to a release position, and simultaneously disengaging anticoagulant pump 24 via clutch 76, which might be, for example, an electromagnetic clutch. Independent operation of blood pump 52 is only permitted by clutch 76 when it is in its reverse mode. In the forward mode of blood pump 52, clutch 72 automatically closes to insure that anticoagulant pump 24 will be in operation at all times that blood is being withdrawn from the donor. This prevents any possibility of withdrawing blood, but not simultaneously anticoagulating it.

In the return cycle, non-plasma component collects at the bottom of braked centrifuge bowl 62 and is pumped out of center port 60 by the reverse pumping action of blood pump 52. Generally, the return cycle is done with pump 52 in its lower speed position. Sterile air originally displaced from centrifuge bowl 62 to plasma pouch 70 during the withdraw cycle is now returned to bowl 62 as the non-plasma component is pumped therefrom.

Non-plasma component fills monitor pouch 46 on the return cycle. Pressure detector 50 senses undesirable build-ups of pressure in the system, which might be caused, for example, by a restriction at the tip of phlebotomy needle 16. When such pressure is sensed, an appropriate signal is transmitted to control logic 34 which in turn causes blood pump 52 to be either slowed down or stopped until the undesirable pressure build-up is relieved.

Non-plasma component then passes back to bubble detection chamber 36 which provides two safeguards in the return mode. The first is provided by filter 40. Check valve 42 insures that flow in the return mode passes through filter 40 which removes undesirable particulate matter, if there is any present, from blood components before they are returned to the donor. The second safeguard is bubble detector elements, such as sonic transducers 38, which detect entrained gas bubbles in the non-plasma component. If such bubbles are present, a signal is transmitted to control logic 34 which immediately shuts down blood pump 52. It is also desirable to provide visual or sonic alarms which alert technicians that an entrained bubble problem has arisen so that corrective action can be quickly undertaken.

The end of a return cycle is detected by monitor pouch 46 which rises as it is emptied. Eventually, weight detector 48 senses that essentially all non-plasma component has been pumped from centrifuge bown 62, and it transmits a signal to control logic 34 to this effect. At this point, the system is immediately and automatically switched to either another withdraw cycle or a stand-by cycle, depending upon the pre-selected sequence and upon whether the return cycle was the first or a subsequent return cycle.

In a typical plasmapheresis procedure, two withdraw cycles and two return cycles are utilized to collect aseptically about 500 ml. of plasma. At the end of the procedure, phlebotomy needle 16 is removed from the donor and plasma container 70 is disconnected from tubing 68, clamped, and placed in a suitable plasma storage area for later use.

There are certain additional or equivalent components, not shown, which can be employed in a plasmapheresis apparatus of this invention. It is usually desirable, for example, to provide a manual override switch which allows an operator to override the automatic controls at any time. Another item generally included is a fan to circulate room air through the equipment so that blood being processed is not overheated. Similarly, a centrifuge designed to operate without a rotary seal may be used in place of the specific centrifuge illustrated. Those skilled in the art will know, or will be able to ascertain, using no more than routine experimentation, such additional or equivalent components.

The entire plasmapheresis apparatus can be provided as an integrated combination of permanent hardware, disposable software, and anticoagulant solution. The permanent hardware might include the centrifuge, pumps, plasma and monitor pouch weight detectors, monitor pouch pressure sensor, automatic pressure cuff and electrical controls all mounted in a portable cabinet. The disposable software set might be a connected assembly of anticoagulant pouch, phlebotomy needle, pump tube sections for anticoagulant and anticoagulated whole blood, centrifuge bowl and plasma collection pouch.

Figure 2:
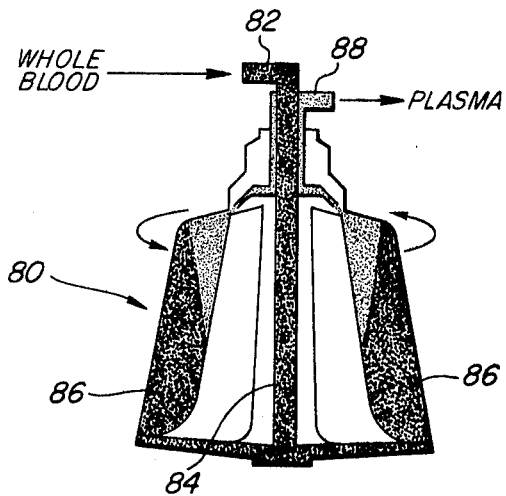
FIG. 2 illustrates the flow of blood components within a centrifuge during a withdraw cycle.
Figure 3:
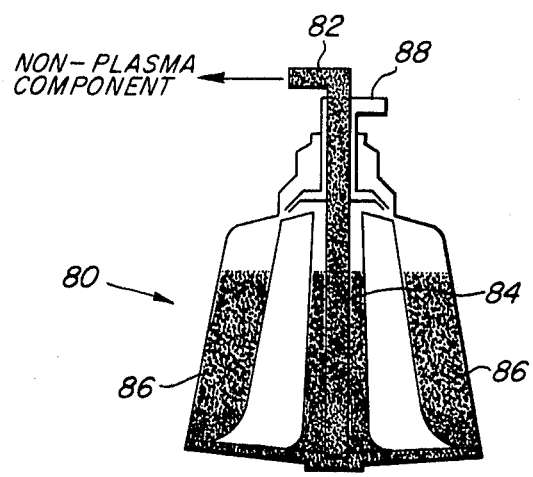
FIG. 3 illustrates the flow of blood components within a centrifuge during a return cycle.

The various flows of whole blood and separated blood components within a centrifuge bowl are illustrated in FIGS. 2 and 3 for a withdraw and return cycle, respectively.

In FIG. 2, whole anticoagulated blood is illustrated flowing to centrifuge 80. The whole blood enters through center port 82 and flows down feed tube stem 84. This blood is then dispensed near the bottom of centrifuge 80 at the center of bowl 86, which is spinning at a speed designed to separate out plasma. The whole blood is forced to the outside by centrifugal force, and as it flows in an upward direction, a distinct plasma phase begins to form about half-way up centrifuge bowl 86. The plasma component is illustrated by the lighter shading. At the top of bowl 86, the plasma component passes through baffled channels and exits through peripheral port 88.

When a predetermined quantity of plasma has been separated, centrifuge bowl 86 is braked to a complete stop causing non-plasma blood component to fall to the bottom of bowl 86 as illustrated in FIG. 3. As previously described, the blood pump is reversed, causing non-plasma component to be pumped out of bowl 86 via center port 82. As previously described, sterile air displaced from the centrifuge bowl during the withdraw cycle is now returned thereto from the plasma pouch.

Figure 4:
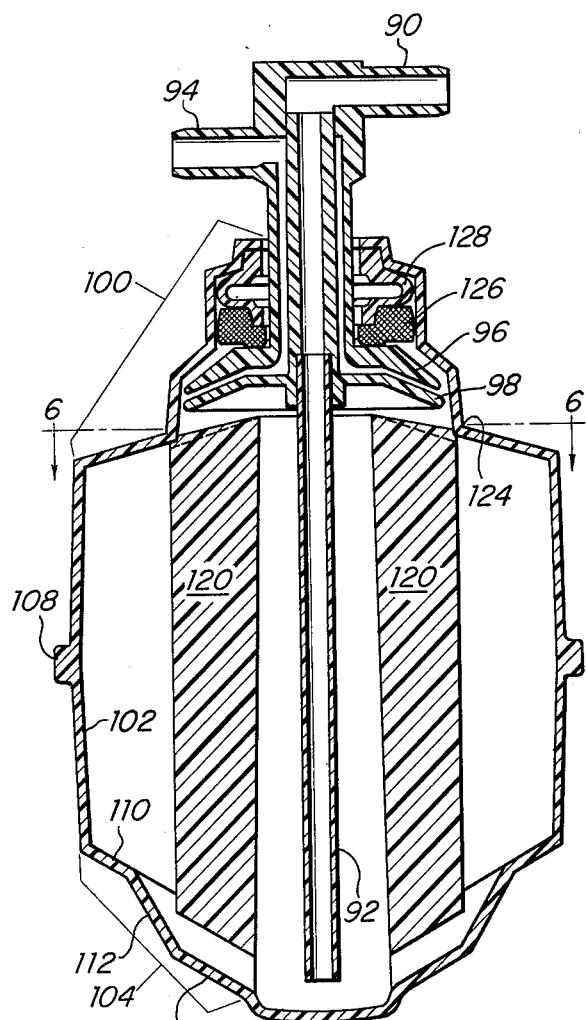
FIGS. 4 and 5 are, respectively, front and side cross-sectional views of a specific centrifuge bowl useful in the plasmapheresis apparatus described herein.
Figure 5:
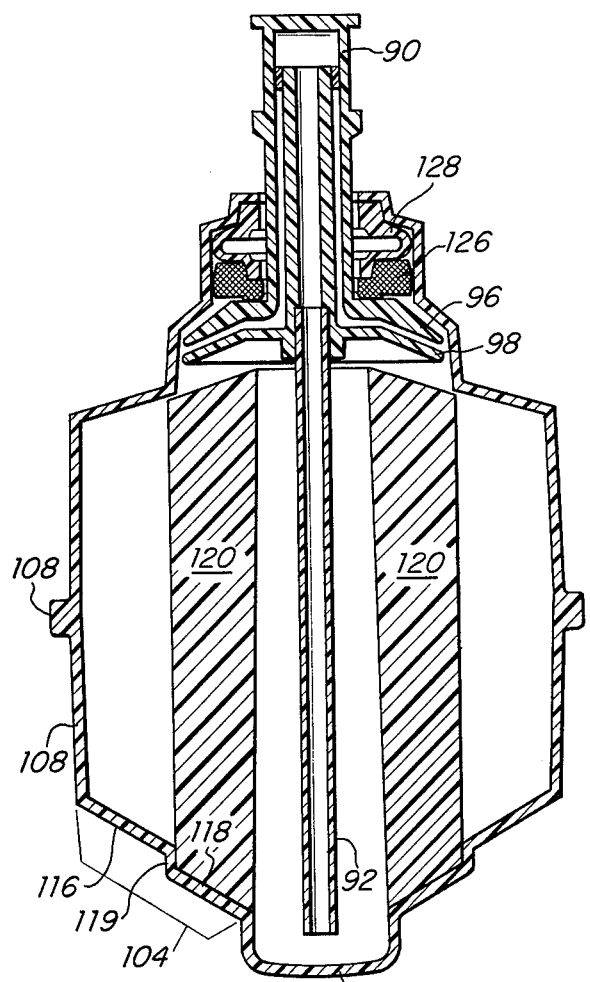
Figure 6:
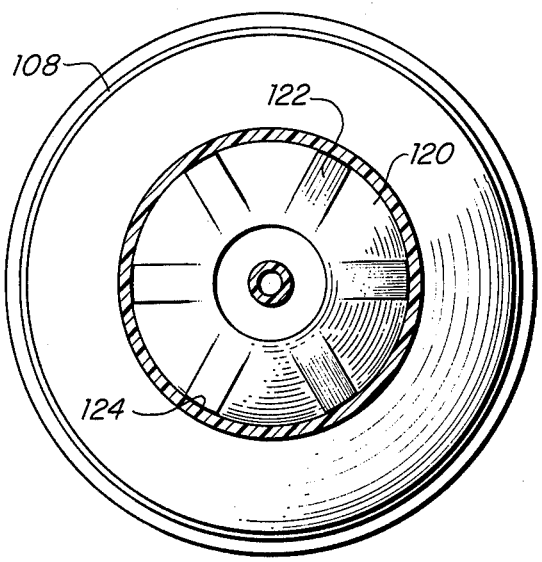
FIG. 6 is a transverse cross-sectional view along line 6—6 of FIG. 4.

A specific embodiment of a new and preferred plasmapheresis centrifuge is illustrated in detail in FIGS. 4–6.

This centrifuge has a central port 90 which is bent at an angle of 90° and leads to feed tube stem 92, which can be either integral with or detachable from central port 90. A peripheral port 94 is provided to allow separated plasma component to flow out of the centrifuge. A channel leading to peripheral port 94 is formed between upper skirt 96 and lower skirt 98 which extend outwardly from a point approximately where central port 90 joins feed tube stem 92. Besides forming part of the outlet channel, lower skirt 98 also provides a splash guard which minimizes intermingling of blood components contained in lower portions of the centrifuge with separated plasma component contained in this section of the centrifuge due to the tremendous dynamic forces applied to the system while the bowl is spinning or braking. The outlet channel formed between upper and lower skirts, 96 and 98, respectively, continues as an annular channel around the periphery of central port 90 until it joins peripheral port 94. Central port 90, feed tube stem 92, peripheral port 94 and skirts 96 and 98 can be suitably fabricated by molding or extrusion techniques from blood compatible plastics such as styrene, ABS, polycarbonate, polyethylene, polyurethane, etc. The ports, skirts, rotary seal, etc., are part of a subassembly which remains stationary while the centrifuge bowl rotates.

The centrifuge bowl is formed from an integrally molded series of outer wall members which can be functionally described by dividing these into four basic zones. Thus, there is an inclined upper wall member 100, a substantially vertical central wall member 102, a lower steeply inclined wall member 104, and a recessed bottom wall member 106.

Upper wall member 100 serves to join the upper extremity of central wall member 102 to non-rotating parts of the centrifuge such as the outer wall of peripheral port 94. It contacts the outer wall of peripheral port 94 at a point above the location of skirts 96 and 98 and a rotary seal to be described infra. As can be seen, upper wall member 100 is actually formed from a series of short wall members joined at various angles to form an appropriate outer housing for components at the top of the centrifuge.

Central wall member 102 defines the outer boundary of an annular-shaped sedimentation space. At approximately its midpoint, a raised joint 103 is present where two halves of the bowl, which have been separately injection molded, are joined. In practice, shoes are positioned and held around the centrifuge bowl and these shoes serve to support the walls of the bowl.

The shape of lower inclined portion 104 is an important feature of the centrifuge bowl because of the importance of minimizing retention of a donor's non-plasma component in the bowl at the conclusion of the return cycle. As will be noted by referring to FIGS. 4 and 5, lower inclined portion 104 is asymmetrical when viewed transversely. In the cross-sectional view shown in FIG. 4, lower portion 104 has three integrally joined, inclined short wall members, namely 110, 112 and 114. Inclined wall member 110 is relatively short and joins wall member 112 which is very steeply pitched, e.g., 45°. Wall member 114 is somewhat less steeply inclined, but still significantly steeped, e.g., 30°, these angles being measured from the horizontal. The cross-sectional view in FIG. 5 is taken transverse to that of FIG. 4, and as can be seen, lower inclined portion 104 in FIG. 5 has two inclined wall members, 116 and 118, which are joined by a short vertical member 119.

The geometrical arrangement illustrated for lower inclined portion 104 provides several features. Because of the extremely steep pitch, which should always be at least 30°, non-plasma component retained in the centrifuge at the end of a separation drains to bottom portion 106 exceptionally well thereby assuring that all blood components except the separated and stored plasma are returned to the donor. The asymmetrical construction also provides generous passageways, at least about 3/16 inch wide, for flow from bottom portion 106 to the sedimentation area housed behind center portion 102. As can be seen in FIG. 4, the minimum passageway occurs between inclined wall member 112 and centrifuge core 120, and this is the point which must have a minimum clearance of about 3/16 inch. The asymmetrical construction also provides an area for the support of core 120 which can be seen in FIG. 5 as the area where core 120 rests upon inclined wall member 118. The geometry of the bowl at its bottom also allows the bowl to accept high flow rates without cell spillage.

Centrifuge core 120 can be conveniently fabricated in one piece by injection molding from foamed polyethylene or other materials. A plan view of the top of core 120 is illustrated in FIG. 6 showing vanes 122. These have steps 124 at their extremities which are used to accurately position core 120 by seating part of upper housing portion 100 against them. When this is done, vanes 122 also serve to provide a narrow flow channel from the sedimentation area of the centrifuge which leads to the outlet channel formed between skirts 96 and 98. This narrow flow channel, coupled with the relative high placement of skirt 98 above the sedimentation space, helps to prevent material from splashing from the sedimentation area into the outlet channels as the bowl brakes and stops.

In practice, the centrifuge bowl spins rapidly while other components of the centrifuge remain stationary. A rotary seal is formed from carbon ring 126 and elastomeric bellows 128. Bellows 128 provides a leak tight seal and also supplies torsional resistance to prevent carbon ring 126 from rotating. The lower surface of carbon ring 126 can be lapped as can the upper surface of skirt 96 to provide outstanding sealing contact. Skirt 96 can be fabricated from a material such as hard anodized aluminum. Suitable rotary seals of this type are described in more detail in U.S. Pat. Nos. 3,409,213 and 3,565,330 to Latham.

Figure 7:
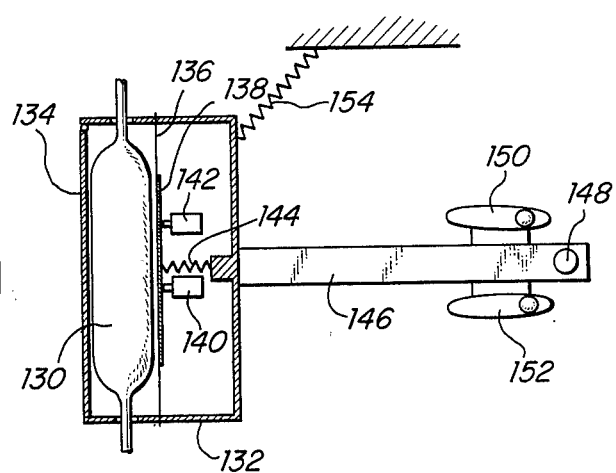
FIG. 7 is a perspective view of a monitor pouch with associated weight and pressure-sensing elements.

FIG. 7 illustrates a cutaway view of a suitable apparatus capable of serving as both a weight and pressure detector for use with a monitor pouch. Monitor pouch 130, shown expanded as it would be when it is filled, can be a thin-walled distendable plastic pouch having bottom and top ducts. The walls of pouch 130 are purposely fabricated to be somewhat flabby — this reduces the possibility that the walls of the pouch will close tightly to form a constriction in the flow path of the system. Pouch 130 is mounted with a housing 132 having a hinged door 134. A flexible membrane 136 having a stiff metal platen 138 attached to its rear is positioned within housing 132 in a contiguous relationship to the side of pouch 130 opposite to hinged door 134. The dimensions should be such that pouch 130 is capable of expanding when it is filled under pressure well beyond the available space between door 134 and membrane 136, so that it forces membrane 136 outwardly. This causes metal platen 138 to contact one or both of double throw microswitches 140 and 142. When platen 138 contacts microswitches 140 and 142, an electrical circuit is closed which causes a signal representative of the pressure within pouch 130 to be transmitted to control logic 34. Spring member 144 is attached to the center of metal platen 138 and provides a means for adjusting the pressure required to close the microswitches. As can be seen, microswitch 140 is positioned fairly closely to the center of platen 138 whereas microswitch 142 is positioned more towards an extremity.

Housing 132 is attached to a balance arm 146 which is pivotally mounted to supporting structure by pin 148. Two mercury switches, 150 and 152 are attached to are 146 so that they are inclined at slightly different angles. These are used to detect the weight of blood or non-plasma component in monitor pouch 130. Alternatively, magnetic reed switches could be used to sense the weight of pouch 130.

Those skilled in the art will recognize many equivalents to the specific embodiments described herein. For example, a membrane filter could be used in place of a centrifuge as the means for separating whole blood into plasma and non-plasma components. Such equivalents are part of this invention and are intended to be covered by the following claims.

What is claimed is:

1. Plasmapheresis apparatus, comprising, in combination:
    means for withdrawing whole blood from a donor;
    means for supplying anticoagulant to said withdrawn whole blood;
    means for separating anticoagulated whole blood into plasma and non-plasma components;
    means for transporting anticoagulated, withdrawn, whole blood to said means for separating;
    a plasma container for receiving plasma from said means for separating;
    means for detecting when a predetermined quantity of separated plasma component has been introduced into said plasma container;
    means for returning non-plasma components from said means for separating to said donor;
    means for monitoring when said non-plasma components have been returned to said donor; and,
    cycle control means for immediately switching from a withdraw cycle to a return cycle in response to said means for detecting and for immediately switching from a return cycle to a withdraw or stand-by cycle in response to said means for monitoring.

2. Plasmapheresis apparatus of claim 1 wherein said means for separating whole blood comprises a centrifuge.

3. Plasmapheresis apparatus of claim 2 wherein said means for monitoring comprises a monitor pouch formed from a flexible material capable of being distended under slight positive pressure and a weight sensor associated therewith for determining the weight of the contents of said monitor pouch.

4. Plasmapheresis apparatus of claim 3 wherein said means for withdrawing includes a phlebotomy needle and pressure cuff.

5. Plasmapheresis apparatus of claim 4 wherein said means for supplying anticoagulant comprises a supply of anticoagulant, an anticoagulant pump, and associated tubing connecting said supply to said pump and said pump to said phlebotomy needle.

6. Plasmapheresis apparatus of claim 5 wherein said means for transporting and said means for returning comprise a blood pump capable of operation in both forward and reverse modes, said blood pump having its inlet side connected by suitable tubing to the monitor pouch and its outlet side connected by suitable tubing to the centrifuge.

7. Plasmapheresis apparatus of claim 6 additionally including means to detect entrained gas bubbles within blood components being returned to a donor.

8. Plasmapheresis apparatus of claim 7 wherein said bubble means to detect includes a blood filter which is by-passable when the plasmapheresis apparatus is in a withdraw cycle.

9. A plasmapheresis centrifuge for separating whole blood into a plasma component and a non-plasma component, comprising, in combination:
    a rotatable centrifuge bowl formed from four integrally connected wall members consisting of an upper inclined wall member, a substantially vertical central wall member, a steeply pitched lower wall member, and a bottom wall member;
    a central core which defines a sedimentation area between said central core and the central wall member of said centrifuge bowl;
    inlet port means for admitting whole blood to said centrifuge bowl;
    outlet port means for removing separated plasma component from said centrifuge; and,
    rotary seal means for sealing the rotatable centrifuge bowl to stationary components of said centrifuge.

* * * * *

UNITED STATES PATENT AND TRADEMARK OFFICE
CERTIFICATE OF CORRECTION

PATENT NO. : 4,086,924
DATED : May 2, 1978
INVENTOR(S) : Allen Latham, Jr.

It is certified that error appears in the above–identified patent and that said Letters Patent are hereby corrected as shown below:

Cancel Claim 9.

On the title page after the abstract, "9 Claims" should read -- 8 Claims --.

Signed and Sealed this

Twenty-fifth Day of March 1980

[SEAL]

Attest:

SIDNEY A. DIAMOND

Attesting Officer

Commissioner of Patents and Trademarks